(12) United States Patent
Nettekoven et al.

(10) Patent No.: US 7,786,143 B2
(45) Date of Patent: Aug. 31, 2010

(54) THIAZOLYL PIPERIDINE DERIVATIVES

(75) Inventors: Matthias Heinrich Nettekoven, Grenzach-Wyhlen (DE); Olivier Roche, Folgensbourg (FR)

(73) Assignee: Hoffman-La Roche Inc., Nutley, NJ (US)

( * ) Notice: Subject to any disclaimer, the term of this patent is extended or adjusted under 35 U.S.C. 154(b) by 921 days.

(21) Appl. No.: 11/502,552

(22) Filed: Aug. 10, 2006

(65) Prior Publication Data
US 2007/0043083 A1 Feb. 22, 2007

(30) Foreign Application Priority Data
Aug. 18, 2005 (EP) ................... 05107586

(51) Int. Cl.
*A61K 31/454* (2006.01)
*C07D 417/14* (2006.01)
(52) U.S. Cl. ...................... 514/326; 546/209
(58) Field of Classification Search ............... 514/326; 546/209
See application file for complete search history.

(56) References Cited

U.S. PATENT DOCUMENTS

| | | | |
|---|---|---|---|
| 4,598,089 A | 7/1986 | Hadvary et al. | |
| 4,931,463 A | 6/1990 | Barbier et al. | |
| 4,983,746 A | 1/1991 | Barbier et al. | |
| 5,175,186 A | 12/1992 | Barbier et al. | |
| 5,246,960 A | 9/1993 | Barbier et al. | |
| 5,399,720 A | 3/1995 | Karpf et al. | |
| 6,004,996 A | 12/1999 | Shah et al. | |
| 6,699,860 B2 * | 3/2004 | Ladouceur et al. | 514/233.5 |

FOREIGN PATENT DOCUMENTS

| | | |
|---|---|---|
| EP | 0 189 577 | 12/1989 |
| EP | 0 185 359 | 12/1991 |
| EP | 0 524 495 | 10/1996 |
| EP | 0 443 449 | 5/1997 |
| FR | 2865733 | 8/2005 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 03/040107 | 5/2003 |
| WO | WO 03/062232 | 7/2003 |
| WO | WO 2005/003128 | 1/2005 |

OTHER PUBLICATIONS

Kuroyan et al. "Synthesis of thiazoles of the piperidine series" CA 100:68213 (1984).*
Harnett et al. "Preparation of thiazole . . . " CA 139:149622 (2003).*
Kido et al. "Anti influencza . . . " CA 148:24385 (2007).*
Kuroyan,R.A.et al., Armyanskii Khimicheskii Zhurnal 36(9); (1983) 610-614 XP008073820.
Burks 1994 in Johnson L.R. ed., Physiology of the Gastrointestinal Tract, Raven Press, NY, pp. 211-242.
Leurs et al., Br J. Pharmacol. 1991, 102, pp. 179-185.
Raithel et al., Int. Arch. Allergy Immunol. 1995, 108, 127-133.
Panula et al., Proc. Natl. Acad. Sci. USA 1984, 81, 2572-2576.
Inagaki et al., J. Comp. Neurol 1988, 273, 283-300.
Arrang et al., Nature 1983, 302, 832-837.
Arrang et al., Neuroscience 1987, 23, 149-157.
Clapham & Kilpatrik, Br. J. Pharmacol. 1982, 107, 919-923.
Blandina et al. in The Histamine H3 Receptor (Leurs RL and Timmermann H eds, 1998, pp. 27-40, Elsevier, Amsterdam, The Netherlands.
Masaki et al; Endocrinol. 2003, 144, 2741-2748.
Hancock et al., European J. of Pharmacol. 2004, 487, 183-197.
Timmermann, J. Med. Chem. 1990, 33, 4-11.
Takahashi, K, Tokita, S., Kotani, H. (2003) J. Pharmacol. Exp. Therapeutics 307, 213-218.
Cheng, Y, Prusoff, WH (1973) Biochem Pharmacol 22, 3099-3108.

* cited by examiner

*Primary Examiner*—Celia Chang
(74) *Attorney, Agent, or Firm*—George W. Johnston; Dennis P. Tramaloni; Brian C. Remy

(57) ABSTRACT

The present invention relates to compounds of formula I

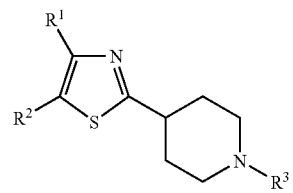

wherein $R^1$, $R^2$ and $R^3$ are as defined in the description and claims. It further relates to pharmaceutically acceptable salts thereof as well as to pharmaceutical compositions comprising these compounds and to methods for their preparation. The compounds are useful for the treatment and/or prevention of diseases which are associated with the modulation of H3 receptors.

17 Claims, No Drawings

THIAZOLYL PIPERIDINE DERIVATIVES

PRIORITY TO RELATED APPLICATIONS

This application claims the benefit of European Application No. 05107586.9, filed Aug. 18, 2005, which is hereby incorporated by reference in its entirety.

FIELD OF THE INVENTION

The present invention is concerned with novel thiazol-2-yl-piperidine derivatives, their manufacture, pharmaceutical compositions containing them and their use as medicaments. The active compounds of the present invention are useful in treating obesity and other disorders.

In particular, the present invention relates to compounds of the general formula

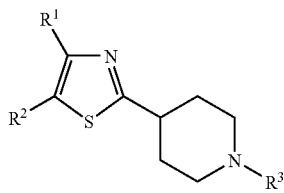

and pharmaceutically acceptable salts thereof.

The compounds of formula I are antagonists and/or inverse agonists at the histamine 3 receptor (H3 receptor).

All documents cited or relied upon below are expressly incorporated herein by reference.

BACKGROUND

Histamine (2-(4-imidazolyl)ethylamine) is one of the aminergic neurotransmitters which is widely distributed throughout the body, e. g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2, H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

SUMMARY OF THE INVENTION

In one embodiment of the present invention, provided is a compound of the formula:

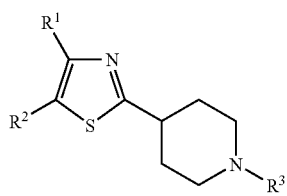

wherein
  $R^1$ is selected from the group consisting of
    phenyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, tetrahydronaphthalenyl unsubstituted or substituted with one to four groups independently selected from the group consisting of lower alkyl, halogen, lower halogenalkyl, lower alkoxy, lower halogenalkoxy, cyano, pyrrolyl and lower hydroxyalkyl;
    benzo[1,3]dioxolyl,
    benzo[1,4]dioxepinyl,
    cycloalkyl,
    pyridyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, pyrazinyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, thienyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, and —CO—NR$^4$R$^5$, wherein R$^4$ is hydrogen or lower alkyl, R$^5$ is phenyl unsubstituted or substituted with one or two groups independently selected from the group consisting of lower alkyl, halogen, lower alkoxy and lower hydroxyalkyl, or R$^4$ and R$^5$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen;

R$^2$ is hydrogen or lower alkyl;

R$^3$ is C$_3$-C$_8$-alkyl or cycloalkyl;

and pharmaceutically acceptable salts thereof.

In another embodiment of the present invention, provided is a process for the manufacture of a compound according to formula I, comprising the steps of:

reacting a compound of the formula II

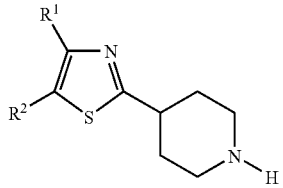

wherein R$^1$ and R$^2$ are as defined above, with an aldehyde or ketone of the formula III

       III wherein R' is C$_1$-C$_7$-alkyl and R" is C$_1$-C$_6$-alkyl or hydrogen or wherein R' and R" together with the C atom they are attached to form a cycloalkyl ring, to obtain a compound of the formula I

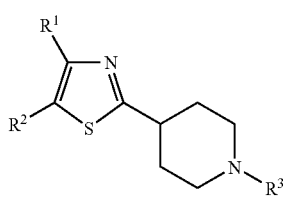

wherein R$^1$, R$^2$ and R$^3$ are as defined above, and if desired, converting the compound obtained into a pharmaceutically acceptable salt.

In a further embodiment of the present invention, provided is a process for the manufacture of a compound according to formula I, wherein R$^1$ is —CO—NR$^4$R$^5$ and R$^4$ and R$^5$ are as defined above, comprising the steps of:

coupling a compound of the formula IV

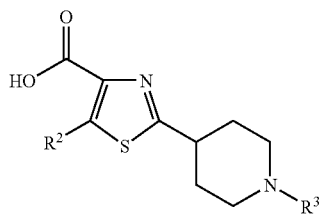

wherein R$^2$ and R$^3$ are as defined above, with an amine of formula V

       V wherein R$^4$ and R$^5$ are as defined above, to obtain a compound of the formula I-A

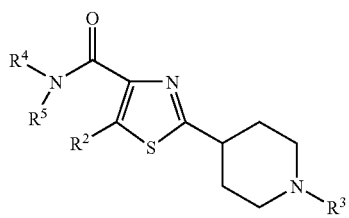

wherein R$^1$ to R$^5$ are as defined above, and if desired, converting the compound obtained into a pharmaceutically acceptable salt.

In a still another embodiment of the present invention, provided is a pharmaceutical composition, comprising a therapeutically effective amount of a compound according to formula I and a pharmaceutically acceptable carrier and/or adjuvant.

In a yet further embodiment of the present invention, provided is a method for the treatment and/or prevention of diseases which are associated with the modulation of H3 receptors, comprising the step of administering a therapeutically effective amount of a compound according to formula I to a human being or animal in need thereof.

In a still further embodiment of the present invention, provided is a method for the treatment or prevention of obesity in a human being or animal, comprising the step of administering to said human being or animal in need thereof a therapeutically effective amount of a compound according to formula I in combination or association with a therapeutically effective amount of a compound selected from the group consisting of a lipase inhibitor, an anorectic agent, a selective serotonin reuptake inhibitor, and an agent that stimulates metabolism of body fat.

In a yet another embodiment of the present invention, provided is a method of treatment or prevention of type II diabetes in a human being or animal, comprising the step of administering to said human being or animal in need thereof a therapeutically effective amount of a compound according to formula I in combination or association with a therapeutically effective amount of an anti-diabetic agent.

DETAILED DESCRIPTION

The invention provides for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_8$-alkyl", alone or in combination, signifies a straight-chain or branched-chain alkyl group with 1 to 8 carbon atoms, preferably a straight or branched-chain alkyl group with 1 to 6 carbon atoms and particularly preferred a straight or branched-chain alkyl group with 1 to 4 carbon atoms Examples of straight-chain and branched $C_1$-$C_8$ alkyl groups are methyl, ethyl, propyl, isopropyl, butyl, isobutyl, tert-butyl, the isomeric pentyls, the isomeric hexyls, the isomeric heptyls and the isomeric octyls, preferably methyl and ethyl and most preferred methyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclopentyl and cyclohexyl with cyclopentyl being particularly preferred.

The term "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.butoxy, preferably methoxy and ethoxy and most preferred methoxy.

The term "alkylsulfonyl" or "lower alkylsulfanyl" refers to the group R'—S(O)$_2$-, wherein R' is lower alkyl and the term "lower alkyl" has the previously given significance. Examples of alkylsulfonyl groups are e.g. methylsulfonyl or ethylsulfonyl.

The term "halogen" refers to fluorine, chlorine, bromine and iodine, with fluorine, chlorine and bromine being preferred.

The term "lower halogenalkyl" or "halogen-$C_{1-8}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "lower halogenalkoxy" or "halogen-$C_{1-8}$-alkoxy" refers to lower alkoxy groups as defined above wherein at least one of the hydrogen atoms of the lower alkoxy group is replaced by a halogen atom, preferably fluoro or chloro, most preferably fluoro. Among the preferred halogenated lower alkyl groups are trifluoromethoxy, difluoromethoxy, fluormethoxy and chloromethoxy, with trifluoromethoxy being especially preferred.

The term "lower hydroxyalkyl" or "hydroxy-$C_{1-8}$-alkyl" refers to lower alkyl groups as defined above wherein at least one of the hydrogen atoms of the lower alkyl group is replaced by a hydroxy group. Examples of lower hydroxyalkyl groups are hydroxymethyl or hydroxyethyl.

The term "dialkylamino" refers to the group —NR'R", wherein R' and R" are lower alkyl and the term "lower alkyl" has the previously given significance. A preferred dialkylamino group is dimethylamino.

The term "form a 4-, 5-, 6- or 7-membered saturated heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. The heteroyclic ring may be unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino. The heterocyclic ring may also be condensed with a phenyl ring, said phenyl ring being unsubstituted or substituted by one, two or three groups independently selected from lower alkyl, lower alkoxy and halogen. An example for such a condensed heterocyclic ring is 3,4-dihydro-1H-isoquinoline.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

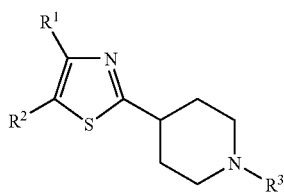

I wherein $R^1$ is selected from the group consisting of phenyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, tetrahydronaphthalenyl unsubstituted or substituted with one to four groups independently selected from the group consisting of lower alkyl, halogen, lower halogenalkyl, lower alkoxy, lower halogenalkoxy, cyano, pyrrolyl and lower hydroxyalkyl;

benzo[1,3]dioxolyl, benzo[1,4]dioxepinyl, cycloalkyl, pyridyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, pyrazinyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, thienyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, and —CO—NR$^4$R$^5$, wherein $R^4$ is hydrogen or lower alkyl, $R^5$ is phenyl unsubstituted or substituted with one or two groups independently selected from the group consisting of lower alkyl, halogen, lower alkoxy and lower hydroxyalkyl, or $R^4$ and $R^5$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen;

$R^2$ is hydrogen or lower alkyl;

$R^3$ is $C_3$-$C_8$-alkyl or cycloalkyl;

and pharmaceutically acceptable salts thereof.

In one embodiment, the invention relates to compounds of formula I, wherein $R^1$ is selected from the group consisting of phenyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, tetrahydronaphthalenyl unsubstituted or substituted with one to four groups independently selected from the group consisting of lower alkyl, halogen, lower halogenalkyl, lower alkoxy, lower halogenalkoxy, cyano, pyrrolyl and lower hydroxyalkyl;

benzo[1,3]dioxolyl, benzo[1,4]dioxepinyl, cycloalkyl, pyridyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, pyrazinyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl, and thienyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl.

Preferred compounds of formula I of the present invention are compounds of formula I, wherein $R^1$ is phenyl unsubstituted or substituted with one or two groups independently selected from the group consisting of lower alkyl, halogen, lower halogenalkyl, lower alkoxy, lower halogenalkoxy, cyano, pyrrolyl and lower hydroxyalkyl.

More preferred are compounds of formula I, wherein $R^1$ is phenyl substituted with one or two groups independently selected from the group consisting of lower alkyl, halogen, lower halogenalkyl, lower alkoxy, lower halogenalkoxy, cyano, pyrrolyl and lower hydroxyalkyl.

Especially preferred are compounds of formula I, wherein $R^1$ is phenyl substituted with one or two groups independently selected from the group consisting of halogen, lower alkoxy, lower halogenalkoxy and pyrrolyl, with those compounds, wherein $R^1$ is phenyl substituted with one or two groups selected from lower alkoxy or lower halogenalkoxy, being most preferred.

In a further embodiment, the invention relates to compounds of formula I as described herein before, wherein $R^1$ is —CO—NR$^4$R$^5$ and wherein $R^4$ is hydrogen or lower alkyl, $R^5$ is phenyl unsubstituted or substituted with one or two groups independently selected from the group consisting of lower alkyl, halogen, lower alkoxy and lower hydroxyalkyl, or $R^4$ and $R^5$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen.

Especially preferred are those compounds of formula I, wherein $R^1$ is —CO—$NR^4R^5$ and wherein $R^4$ and $R^5$ together with the nitrogen atom to which they are attached form a 4-, 5-, 6- or 7-membered saturated or partly unsaturated heterocyclic ring optionally containing a further heteroatom selected from nitrogen, oxygen or sulfur, said saturated heterocyclic ring being unsubstituted or substituted by one, two or three groups independently selected from the group consisting of lower alkyl, halogen, halogenalkyl, hydroxy, lower hydroxyalkyl, lower alkoxy, oxo, phenyl, benzyl, pyridyl, dialkylamino, carbamoyl, lower alkylsulfonyl, and lower halogenalkylcarbonylamino, or being condensed with a phenyl ring, said phenyl ring being unsubstituted or substituted by one, two or three groups independently selected from lower alkyl, lower alkoxy and halogen.

Even more preferably, $R^4$ and $R^5$ together with the nitrogen atom to which they are attached form a heterocyclic ring selected from the group consisting of morpholine, piperidine, azepane, pyrrolidine, azetidine and 3,4-dihydro-1H-isoquinoline, wherein the ring is unsubstituted or substituted by lower alkyl.

Also preferred are compounds of formula I, wherein $R^1$ is —CO—$NR^4R^5$ and wherein $R^4$ is hydrogen and $R^5$ is phenyl unsubstituted or substituted with one or two groups independently selected from the group consisting of lower alkyl, halogen, lower alkoxy and lower hydroxyalkyl, with those compounds wherein $R^5$ is phenyl substituted by halogen or lower alkoxy being especially preferred.

Furthermore, compounds of formula I according to the present invention are preferred, wherein $R^2$ is hydrogen.

Also preferred are compounds of formula, wherein $R^2$ is lower alkyl, with those compounds wherein $R^2$ is methyl being especially preferred.

Another group of preferred compounds of formula I are those, wherein $R^3$ is $C_3$-$C_8$-alkyl.

Especially preferred are compounds of formula I, wherein $R^3$ is isopropyl or isobutyl.

Also preferred are compounds of formula I, wherein $R^3$ is cycloalkyl, with those compounds, wherein $R^3$ is cyclopentyl being especially preferred.

Examples of preferred compounds of formula I are the following:

isopropyl-4-(4-phenyl-thiazol-2-yl)-piperidine,
cyclopentyl-4-(4-phenyl-thiazol-2-yl)-piperidine,
4-[4-(3,4-difluoro-phenyl)-thiazol-2-yl]-1-isobutyl-piperidine,
4-[4-(3,4-difluoro-phenyl)-thiazol-2-yl]-1-isopropyl-piperidine,
cyclopentyl-4-[4-(3,4-difluoro-phenyl)-thiazol-2-yl]-piperidine,
4-(4-cyclohexyl-thiazol-2-yl)-1-isobutyl-piperidine,
4-(4-cyclohexyl-thiazol-2-yl)-1-cyclopentyl-piperidine,
isobutyl-4-[4-(4-methoxy-phenyl)-thiazol-2-yl]-piperidine,
isopropyl-4-[4-(4-methoxy-phenyl)-thiazol-2-yl]-piperidine,
cyclopentyl-4-[4-(4-methoxy-phenyl)-thiazol-2-yl]-piperidine,
4-[4-(2-fluoro-4-methoxy-phenyl)-thiazol-2-yl]-1-isobutyl-piperidine,
4-[4-(2-fluoro-4-methoxy-phenyl)-thiazol-2-yl]-1-isopropyl-piperidine
cyclopentyl-4-[4-(2-fluoro-4-methoxy-phenyl)-thiazol-2-yl]-piperidine,
isobutyl-4-[4-(2-methoxy-phenyl)-thiazol-2-yl]-piperidine,
isopropyl-4-[4-(2-methoxy-phenyl)-thiazol-2-yl]-piperidine,
cyclopentyl-4-[4-(2-methoxy-phenyl)-thiazol-2-yl]-piperidine,
2-[2-(1-isobutyl-piperidine-4-yl)-thiazol-4-yl]-3-methyl-pyrazine,
2-[2-(1-cyclopentyl-piperidin-4-yl)-thiazol-4-yl]-3-methyl-pyrazine,
isobutyl-4-[4-(2-trifluoromethyl-phenyl)-thiazol-2-yl]-piperidine,
cyclopentyl-4-[4-(2-trifluoromethyl-phenyl)-thiazol-2-yl]-piperidine,
4-[4-(4-chloro-phenyl)-thiazol-2-yl]-1-isobutyl-piperidine,
4-[4-(4-chloro-phenyl)-thiazol-2-yl]-1-isopropyl-piperidine,
4-[4-(4-chloro-phenyl)-thiazol-2-yl]-1-cyclopentyl-piperidine,
4-[4-(3-fluoro-phenyl)-thiazol-2-yl]-1-isobutyl-piperidine,
4-[4-(3-fluoro-phenyl)-thiazol-2-yl]-1-isopropyl-piperidine,
cyclopentyl-4-[4-(3-fluoro-phenyl)-thiazol-2-yl]-piperidine,
cyclopentyl-4-(5-methyl-4-phenyl-thiazol-2-yl)-piperidine,
4-[4-(2-fluoro-3-trifluoromethyl-phenyl)-thiazol-2-yl]-1-isopropyl-piperidine,
4-[2-(1-isopropyl-piperidin-4-yl)-thiazol-4-yl]-benzonitrile,
isopropyl-4-[4-(4-trifluoromethyl-phenyl)-thiazol-2-yl]-piperidine,
isopropyl-4-[4-(3-methoxy-phenyl)-thiazol-2-yl]-piperidine,
isopropyl-4-(4-p-tolyl-thiazol-2-yl)-piperidine,
4-[4-(4-difluoromethoxy-phenyl)-thiazol-2-yl]-1-isopropyl-piperidine,
4-[4-(2,3-dihydro-benzo[1,4]dioxin-6-yl)-thiazol-2-yl]-1-isopropyl-piperidine,
4-[4-(3,4-dihydro-2H-benzo[b][1,4]dioxepin-7-yl)-thiazol-2-yl]-1-isopropyl-piperidine,
3-[2-(1-isopropyl-piperidin-4-yl)-thiazol-4-yl]-benzonitrile,
isopropyl-4-[4-(4-pyrrolidin-1-yl-phenyl)-thiazol-2-yl]-piperidine,
isopropyl-4-[4-(4-trifluoromethoxy-phenyl)-thiazol-2-yl]-piperidine,
isopropyl-4-[4-(3-trifluoromethyl-phenyl)-thiazol-2-yl]-piperidine,
4-[4-(3,4-dimethoxy-phenyl)-thiazol-2-yl]-1-isopropyl-piperidine,
4-(4-benzo[1,3]dioxol-5-yl-thiazol-2-yl-1-isopropyl-piperidine,
4-[4-(4-bromo-phenyl)-5-methyl-thiazol-2-yl]-1-isopropyl-piperidine,
isopropyl-4-(4-thiophen-3-yl-thiazol-2-yl)-piperidine,
isopropyl-4-(4-thiophen-2-yl-thiazol-2-yl)-piperidine,
4-[4-(3,4-dichloro-phenyl)-thiazol-2-yl]-1-isopropyl-piperidine,
4-[4-(2,4-dimethoxy-phenyl)-thiazol-2-yl]-1-isopropyl-piperidine,
4-[2-(1-cyclopentyl-piperidin-4-yl)-thiazol-4-yl]-benzonitrile,
cyclopentyl-4-[4-(4-trifluoromethyl-phenyl)-thiazol-2-yl]-piperidine,
cyclopentyl-4-[4-(5,5,8,8-tetramethyl-5,6,7,8-tetrahydro-naphthalen-2-yl)-thiazol-2-yl]-piperidine, cyclopentyl-4-[4-(3-methoxy-phenyl)-thiazol-2-yl]-piperidine,
cyclopentyl-4-[4-(4-difluoromethoxy-phenyl)-thiazol-2-yl]-piperidine,
cyclopentyl-4-[4-(2,3-dihydro-benzo[1,4]dioxin-6-yl)-thiazol-2-yl]-piperidine,
cyclopentyl-4-[4-(3,4-dihydro-2H-benzo[b][1,4]dioxepin-7-yl)-thiazol-2-yl]-piperidine,
3-[2-(1-cyclopentyl-piperidin-4-yl)-thiazol-4-yl]-benzonitrile,
cyclopentyl-4-[4-(4-trifluoromethoxy-phenyl)-thiazol-2-yl]-piperidine,
cyclopentyl-4-[4-(3-trifluoromethyl-phenyl)-thiazol-2-yl]-piperidine,
cyclopentyl-4-[4-(3,4-dimethoxy-phenyl)-thiazol-2-yl]-piperidine,
4-(4-benzo[1,3]dioxol-5-yl-thiazol-2-yl-1-cyclopentyl-piperidine,
4-[4-(4-bromo-phenyl)-5-methyl-thiazol-2-yl]-1-cyclopentyl-piperidine,
4-[2-(1-cyclopentyl-piperidin-4-yl)-thiazol-4-yl]-pyridine,
cyclopentyl-4-(4-thiophen-3-yl-thiazol-2-yl)-piperidine,
cyclopentyl-4-[4-(3,4-dichloro-phenyl)-thiazol-2-yl]-piperidine,
cyclopentyl-4-[4-(2,4-dimethoxy-phenyl)-thiazol-2-yl]-piperidine,
4-[4-(3,5-bis-trifluoromethyl-phenyl)-thiazol-2-yl]-1-cyclopentyl-piperidine,
2-(1-isopropyl-piperidin-4-yl)-thiazole-4-carboxylic acid (4-chloro-phenyl)-amide,
[2-(1-cyclopentyl-piperidin-4-yl)-thiazol-4-yl]-(2-methyl-pyrrolidin-1-yl)-methanone,
[2-(1-cyclopentyl-piperidin-4-yl)-thiazol-4-yl]-(3-methyl-piperidin-1-yl)-methanone,
[2-(1-cyclopentyl-piperidin-4-yl)-thiazol-4-yl]-(2-methyl-piperidin-1-yl)-methanone,
azepan-1-yl-[2-(1-cyclopentyl-piperidin-4-yl)-thiazol-4-yl]-methanone,
[2-(1-cyclopentyl-piperidin-4-yl)-thiazol-4-yl]-(3,4-dihydro-1H-isoquinolin-2-yl)-methanone,
2-(1-cyclopentyl-piperidin-4-yl)-thiazole-4-carboxylic acid phenylamide,
2-(1-cyclopentyl-piperidin-4-yl)-thiazole-4-carboxylic acid (4-chloro-phenyl)-amide,
2-(1-cyclopentyl-piperidin-4-yl)-thiazole-4-carboxylic acid (3-methoxy-phenyl)-amide, and pharmaceutically acceptable salts thereof.

Especially preferred are the following compounds of formula I of the present invention:
isopropyl-4-[4-(4-methoxy-phenyl)-thiazol-2-yl]-piperidine,
cyclopentyl-4-[4-(4-methoxy-phenyl)-thiazol-2-yl]-piperidine,
4-[4-(2-fluoro-4-methoxy-phenyl)-thiazol-2-yl]-1-isopropyl-piperidine
cyclopentyl-4-[4-(2-fluoro-4-methoxy-phenyl)-thiazol-2-yl]-piperidine,
cyclopentyl-4-[4-(2-methoxy-phenyl)-thiazol-2-yl]-piperidine,
4-[4-(4-chloro-phenyl)-thiazol-2-yl]-1-isopropyl-piperidine,
4-[4-(4-chloro-phenyl)-thiazol-2-yl]-1-cyclopentyl-piperidine,
isopropyl-4-[4-(4-pyrrolidin-1-yl-phenyl)-thiazol-2-yl]-piperidine,
4-[4-(3,4-dimethoxy-phenyl)-thiazol-2-yl]-1-isopropyl-piperidine,
4-[4-(2,4-dimethoxy-phenyl)-thiazol-2-yl]-1-isopropyl-piperidine,
cyclopentyl-4-[4-(4-difluoromethoxy-phenyl)-thiazol-2-yl]-piperidine,
4-[4-(4-bromo-phenyl)-5-methyl-thiazol-2-yl]-1-cyclopentyl-piperidine,
cyclopentyl-4-[4-(2,4-dimethoxy-phenyl)-thiazol-2-yl]-piperidine, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of the formula II

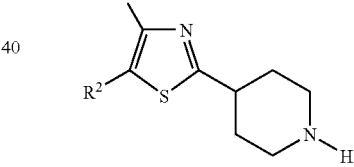

II wherein $R^1$ and $R^2$ are as defined herein before, preferably its hydrobromide salt, with an aldehyde or ketone of the formula III

R'R"C=O    III wherein R' is $C_1$-$C_7$-alkyl and R" is $C_1$-$C_6$-alkyl or hydrogen or wherein R' and R" form together with the C atom they are attached to a cycloalkyl ring, to obtain a compound of the formula I

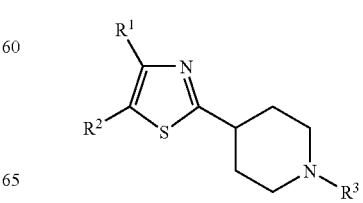

I wherein $R^1$, $R^2$ and $R^3$ are as defined hereinbefore, and if desired, converting the compound obtained into a pharmaceutically acceptable salt.

Preferred intermediate compounds of formula II are the following:

4-(phenylthiazol-2-yl)-piperidine hydrobromide,
4-[4-(3,4-difluoro-phenyl)-thiazol-2-yl]-piperidine hydrobromide,
4-(4-cyclohexyl-thiazol-2-yl)-piperidine hydrobromide,
4-[4-(4-methoxy-phenyl)-thiazol-2-yl]-piperidine hydrobromide,
4-[4-(2-fluoro-4-methoxy-phenyl)-thiazol-2-yl]-piperidine hydrobromide,
4-[4-(2-methoxy-phenyl)-thiazol-2-yl]-piperidine hydrobromide,
2-methyl-3-(2-piperidin-4-yl-thiazol-4-yl)-pyrazine hydrobromide,
4-[4-(2-trifluoromethyl-phenyl)-thiazol-2-yl]-piperidine hydrobromide,
4-[4-(4-chloro-phenyl)-thiazol-2-yl]-piperidine hydrobromide,
4-[4-(3-fluoro-phenyl)-thiazol-2-yl]-piperidine hydrobromide,
4-(5-methyl-4-phenyl-thiazol-2-yl)-piperidine hydrobromide,
4-[4-(2-fluoro-3-trifluoromethyl-phenyl)-thiazol-2-yl]-piperidine hydrobromide,
4-(2-piperidin-4-yl-thiazol-4-yl)-benzonitrile hydrobromide,
4-[4-(4-trifluoromethyl-phenyl)-thiazol-2-yl]-piperidine hydrobromide,
4-[4-(5,5,8,8-tetramethyl-5,6,7,8-tetrahydro-naphthalen-2-yl)-thiazol-2-yl]-piperidine hydrobromide,
4-[4-(3-methoxy-phenyl)-thiazol-2-yl]-piperidine hydrobromide,
4-(4-p-tolyl-thiazol-2-yl)-piperidine hydrobromide,
4-[4-(4-difluoromethoxy-phenyl)-thiazol-2-yl]-piperidine hydrobromide,
4-[4-(2,3-dihydro-benzo[1,4]dioxin-6-yl)-thiazol-2-yl]-piperidine hydrobromide,
4-[4-(3,4-dihydro-2H-benzo[b][1,4]dioxepin-7-yl)-thiazol-2-yl]-piperidine hydrobromide,
3-(2-piperidin-4-yl-thiazol-4-yl)-benzonitrile hydrobromide,
4-[4-(4-pyrrolidin-1-yl-phenyl)-thiazol-2-yl]-piperidine hydrobromide,
4-[4-(4-trifluoromethoxy-phenyl)-thiazol-2-yl]-piperidine hydrobromide,
4-[4-(3-trifluoromethyl-phenyl)-thiazol-2-yl]-piperidine hydrobromide,
4-[4-(3,4-dimethoxy-phenyl)-thiazol-2-yl]-piperidine hydrobromide,
4-(4-benzo[1,3]dioxol-5-yl-thiazol-2-yl)-piperidine hydrobromide,
4-[4-(4-bromo-phenyl)-5-methyl-thiazol-2-yl]-piperidine hydrobromide,
4-(2-piperidin-4-yl-thiazol-4-yl)-pyridine dihydrobromide,
4-(4-thiophen-3-yl-thiazol-2-yl)-piperidine hydrobromide,
4-(4-thiophen-2-yl-thiazol-2-yl)-piperidine hydrobromide,
4-[4-(3,4-dichloro-phenyl)-thiazol-2-yl]-piperidine hydrobromide,
4-[4-(2,4-dimethoxy-phenyl)-thiazol-2-yl]-piperidine hydrobromide, and
4-[4-(3,5-bis-trifluoromethyl-phenyl)-thiazol-2-yl]-piperidine hydrobromide.

A further aspect of the present invention is a process for the manufacture of compounds of formula I as defined above, wherein $R^1$ is —CO—$NR^4R^5$, which process comprises coupling a compound of the formula IV

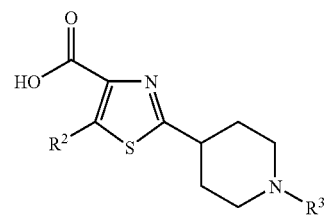

IV wherein $R^2$ and $R^3$ are as defined herein before, with an amine of formula V $R^4R^5N$—H     V wherein $R^4$ and $R^5$ are as defined herein before, to obtain a compound of the formula I-A

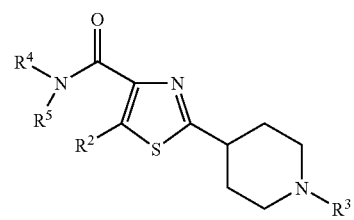

I-A wherein $R^1$ to $R^5$ are as defined hereinbefore, and if desired, converting the compound obtained into a pharmaceutically acceptable salt.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given above unless indicated to the contrary.

Compounds of general formula I can be prepared according to scheme 1 as follows: 4-Thiocarbamoyl-piperidine-1-carboxylic acid tert-butyl ester VII (which is commercially available, CAS Registry No. 214834-18-1) can be converted to thiazoles II by various procedures described in the art. However, it is convenient to react VII with α-bromo ketones (which are either commercially available, described previously in the literature or synthetically easily accessible via various routes described in literature) in the presence or absence of a solvent and in the presence or absence of a base. There is no particular restriction on the nature of the solvent to be employed, provided that it has no adverse effect on the reaction or the reagents involved and that it can dissolve the reagents, at least to some extent. Examples for suitable solvents include: ethanol, methanol, dioxane, dimethylformamide and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the thiazole derivatives II or the respective salts thereof.

Scheme 1

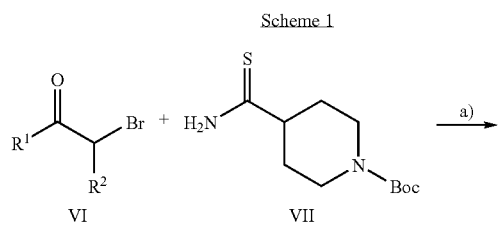

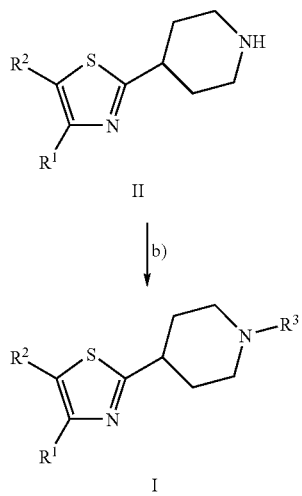

The alkylation of piperidine derivatives II can be carried out by various methods that are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). For the reductive amination reducing agents such as py-BH$_3$ complex, NaBH(OAc)$_3$, NaCNBH$_3$ can be employed under acidic (e.g. acetic acid additive, Ti(iPrO)$_4$, ZnCl$_2$) or under basic conditions (no additive) in a solvent such as dichloromethane (DCM), dichloroethane (DCE), tetrahydrofurane (THF), ethanol or mixtures thereof at ambient or elevated temperatures. It is convenient to react piperidine derivatives II with an excess amount of the appropriate aldehyde or ketone (commercially available) in the presence of an excess amount of NaBH(OAc)$_3$ under acidic conditions (acetic acid). In cases where the piperidines II were reacted with ketones the reaction temperature was shifted from room temperature (used in the cases where piperidines II were reacted with aldehydes) to 40° C.

Compounds of formula I, wherein $R^1$ is —CO—NR$^4$R$^5$, are prepared from ethyl bromopyruvates (VIII) following the method described in scheme 2.

Scheme 2

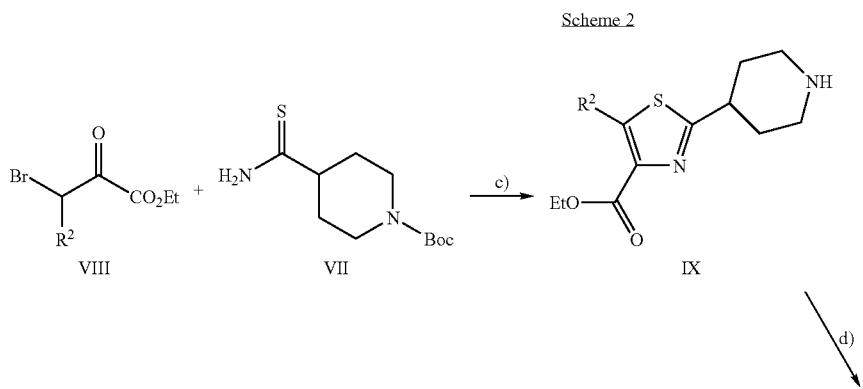

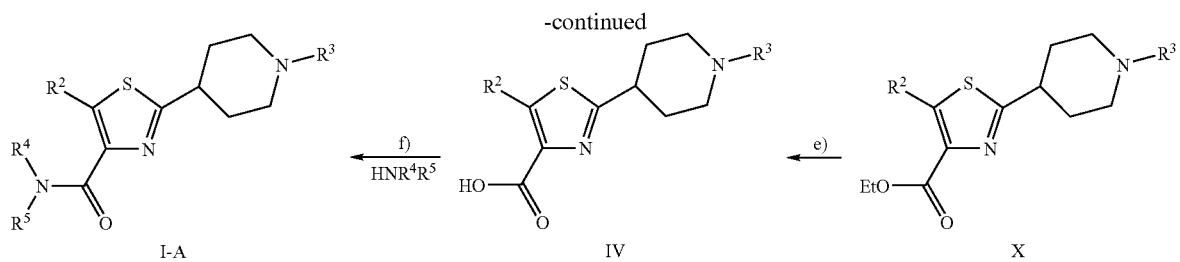

4-Thiocarbamoyl-piperidine-1-carboxylic acid tert-butyl ester VII (commercially available) can be reacted with an ethyl bromopyruvate VIII to obtain the thiazole derivatives IX. There is no particular restriction on the nature of the solvent to be employed, provided that it has no adverse effect on the reaction or the reagents involved and that it can dissolve the reagents, at least to some extent. Examples for suitable solvents include: ethanol, methanol, dioxane and the like. The reaction can take place over a wide range of temperatures, and the precise reaction temperature is not critical to the invention. It is convenient to carry out the reaction with heating from ambient temperature to reflux.

The reductive amination of the piperidine can be carried out as described in step b) above. It is convenient to react the piperidines IX with an excess amount of the appropriate aldehyde or ketone (commercially available) in the presence of an excess amount of NaBH(OAc)$_3$ under acidic conditions (acetic acid). In cases where an piperidine IX is reacted with ketones the reaction temperature was shifted from room temperature (used in the cases where piperidines II were reacted with aldehydes) to 40° C.

The esters of formula X can undergo consecutive reactions like cleavage of the ester moiety of X under various reaction conditions in order to access acid derivatives IV. However, it is convenient to react esters X under acidic conditions in the presence or absence of a solvent. There is no particular restriction on the nature of acids to be employed, provided that they affect the desired reaction. Examples for suitable acids include acetic acid, HCl and the like. There is no particular restriction on the nature of the solvent to be employed, provided that it has no adverse effect on the reaction or the reagents involved and that it can dissolve the reagents, at least to some extent. Examples for suitable solvents or mixtures thereof include: water, THF, dioxane and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the acid derivatives IV.

The coupling of carboxylic acids with amines is widely described in literature and the procedures are known to those in the art (For reaction conditions described in literature affecting such reactions see for example: Comprehensive Organic Transformations: A Guide to Functional Group Preparations, 2nd Edition, Richard C. Larock. John Wiley & Sons, New York, N.Y. 1999). Carboxylic acids IV can conveniently be transformed to the respective amide through coupling with an amine HNR$^4$R$^5$ (V, either commercially available or accessible by methods described in references or by methods known in the art; as appropriate) by employing the usage of coupling reagents. For example coupling agents like N,N'-carbonyldiimidazole (CDI), N,N'-dicyclohexylcarbodiimide (DCC), 1-(3-dimethylaminopropyl)-3-ethylcarbodiimide hydrochloride (EDCI), 1-[bis(dimethylamino)methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyluronium tetrafluoroborate (TBTU) and the like can equally well be employed to affect such transformation. It is convenient to carry out the reaction in a solvent like dimethylformamide (DMF) and in the presence of a base. There is no particular restriction on the nature of the solvent to be employed, provided that it has no adverse effect on the reaction or the reagents involved and that it can dissolve the reagents, at least to some extent. Examples for suitable solvents include: DMF, dichloromethane (DCM), dioxane, THF, and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield amide derivatives I-A.

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Examples of such diseases are obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

The invention also provides for a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to p olymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

The invention also provides for a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like.

Also an embodiment of the invention is the method as described above for the simultaneous, separate or sequential administration of a compound according to formula I and a therapeutically effective amount of a anti-hypertensive agent.

The use of a compound of formula I in the manufacture of a medicament for the treatment and prevention of hypertension in a patient who is also receiving treatment with an anti-hypertensive agent, is also an embodiment of the present invention.

The compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 μg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 μl. The incubation was followed by rapid filtration on GF/B filters (pre-soaked with 100 μl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard top-counter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human HR3-CHO cell line. An appropriate amount of protein, e.g. approximately 500 cpm binding of RAMH at Kd, were incubated for 1 hour at room temperature in 250 µl final volume in 96-well plates in presence of $^3H(R)(\alpha$-Methylhistamine (1 nM final concentration=Kd). Non-specific binding was determined using a 200 fold excess of cold (R)α-Methylhistamine dihydrobromide.

All compounds were tested at a single concentration in duplicates. Compounds that showed an inhibition of $[^3H]$-RAMH by more than 50% were tested again to determine $IC_{50}$ in a serial dilution experiment. Ki's were calculated from $IC_{50}$ based on Cheng-Prusoff equation (Cheng, Y, Prusoff, W H (1973) Biochem Pharmacol 22, 3099-3108).

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 9 | 28 |
| Example 52 | 123 |
| Example 68 | 156 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Example 1

Isopropyl-4-(4-phenyl-thiazol-2-yl)-piperidine

Step 1: 4-(4-Phenyl-thiazol-2-yl)-piperidine hydrobromide (Intermediate 1)

A mixture of 1 g (4.1 mmol) 4-thiocarbamoyl-piperidine-1-carboxylic acid tert-butyl ester (commercially available) and 0.816 g (4.1 mmol) 2-bromo-1-phenyl-ethanone (commercially available) in 10 ml methanol was stirred at 70° C. for 22 h. After evaporation to dryness the residue was suspended in diethyl ether and filtered. The residue washed with diethyl ether and dried under vacuum to yield 1.279 g (96%) of the title compound in white crystalline form. (m/e): 245.2 ($MH^+$(–HBr); 100%).

Step 2: 1-Isopropyl-4-(4-phenyl-thiazol-2-yl)-piperidine

A mixture of 24.5 mg (0.1 mmol) 4-(4-phenyl-thiazol-2-yl)-piperidine hydrobromide, excess acetone and excess sodium triacetoxyborohydride in 1 ml THF and 20 µl acetic acid was stirred at room temperature for 16 h. After addition of 0.2 ml water, 0.2 ml methanol and 0.15 ml $NEt_3$ the mixture was purified by preparative HPLC on reversed phase eluting with a gradient of acetonitrile/water (0.1% $NEt_3$) to yield after evaporation of the product fractions 12.8 mg (45 %) of the title compound. (m/e): 287.3 ($MH^+$; 100%).

According to the procedure described in step 1 for the synthesis of intermediate 1 the further intermediates 2 to 33 were prepared from different starting materials as given in Table 1.

TABLE 1

| Intermediate | Name | Starting materials | MW | MH+ (-HBr) found [100%] |
|---|---|---|---|---|
| 2 | 4-[4-(3,4-difluoro-phenyl)-thiazol-2-yl]-piperidine; hydrobromide | 4-thiocarbamoyl-piperidine-1-carboxylic acid tert-butyl ester (commercially available) and 2-bromo-1-(3,4-difluoro-phenyl)-ethanone (commercially available) | 361.25 | 281.1 |
| 3 | 4-(4-cyclohexyl-thiazol-2-yl)-piperidine; hydrobromide | 4-thiocarbamoyl-piperidine-1-carboxylic acid tert-butyl ester (commercially available) and 2-bromo-1-cyclohexyl-ethanone (Tetrahedron 26, 5611, 1970) | 331.32 | 251.2 |
| 4 | 4-[4-(4-methoxy-phenyl)-thiazol-2-yl]-piperidine; hydrobromide | 4-thiocarbamoyl-piperidine-1-carboxylic acid tert-butyl ester (commercially available) and 2-bromo-1-(4-methoxy-phenyl)-ethanone (commercially available) | 355.30 | 275.2 |
| 5 | 4-[4-(2-fluoro-4-methoxy-phenyl)-thiazol-2-yl]-piperidine; hydrobromide | 4-thiocarbamoyl-piperidine-1-carboxylic acid tert-butyl ester (commercially available) and 2-bromo-1-(2-fluoro-4-methoxy-phenyl)-ethanone (commercially available) | 292.38 | 293.2 |
| 6 | 4-[4-(2-methoxy-phenyl)-thiazol-2-yl]-piperidine; hydrobromide | 4-thiocarbamoyl-piperidine-1-carboxylic acid tert-butyl ester (commercially available) and 2-bromo-1-(2-methoxy-phenyl)-ethanone (commercially available) | 355.30 | 275.2 |
| 7 | 2-methyl-3-(2-piperidin-4-yl-thiazol-4-yl)-pyrazine; hydrobromide | 4-thiocarbamoyl-piperidine-1-carboxylic acid tert-butyl ester (commercially available) and 2-bromo-1-(3-methyl-pyrazin-2-yl)-ethanone (WO 2004/014884) | 341.27 | 261.1 |
| 8 | 4-[4-(2-trifluoromethyl-phenyl)-thiazol-2-yl]-piperidine; hydrobromide | 4-thiocarbamoyl-piperidine-1-carboxylic acid tert-butyl ester (commercially available) and 2-bromo-1-(2-trifluoromethyl-phenyl)-ethanone (commercially available) | 393.27 | 313 |
| 9 | 4-[4-(4-chloro-phenyl)-thiazol-2-yl]-piperidine; hydrobromide | 4-thiocarbamoyl-piperidine-1-carboxylic acid tert-butyl ester (commercially available) and 2-bromo-1-(4-chloro-phenyl)-ethanone (commercially available) | 359.72 | 279.1 |
| 10 | 4-[4-(3-fluoro-phenyl)-thiazol-2-yl]-piperidine; hydrobromide | 4-thiocarbamoyl-piperidine-1-carboxylic acid tert-butyl ester (commercially available) and 2-bromo-1-(3-fluoro-phenyl)-ethanone (commercially available) | 343.26 | 263 |
| 11 | 4-(5-methyl-4-phenyl-thiazol-2-yl)-piperidine; hydrobromide | 4-thiocarbamoyl-piperidine-1-carboxylic acid tert-butyl ester (commercially available) and 2-bromo-1-phenyl-propan-1-one (commercially available) | 339.30 | 259.1 |
| 12 | 4-[4-(2-fluoro-3-trifluoromethyl-phenyl)-thiazol-2-yl]-piperidine; hydrobromide | 4-thiocarbamoyl-piperidine-1-carboxylic acid tert-butyl ester (commercially available) and 2-bromo-1-(2-fluoro-3-trifluoromethyl-phenyl)-ethanone (commercially available) | 411.26 | 331 |

TABLE 1-continued

| Intermediate | Name | Starting materials | MW | MH+ (-HBr) found [100%] |
|---|---|---|---|---|
| 13 | 4-(2-piperidin-4-yl-thiazol-4-yl)-benzonitrile; hydrobromide | 4-thiocarbamoyl-piperidine-1-carboxylic acid tert-butyl ester (commercially available) and 4-(2-bromo-acetyl)-benzonitrile (commercially available) | 350.29 | 270 |
| 14 | 4-[4-(4-trifluoromethyl-phenyl)-thiazol-2-yl]-piperidine; hydrobromide | 4-thiocarbamoyl-piperidine-1-carboxylic acid tert-butyl ester (commercially available) and 2-bromo-1-(4-trifluoromethyl-phenyl)-ethanone (commercially available) | 393.27 | 313.1 |
| 15 | 4-[4-(5,5,8,8-tetramethyl-5,6,7,8-tetrahydro-naphthalen-2-yl)-thiazol-2-yl]-piperidine; hydrobromide | 4-thiocarbamoyl-piperidine-1-carboxylic acid tert-butyl ester (commercially available) and 2-bromo-1-(5,5,8,8-tetramethyl-5,6,7,8-tetrahydro-naphthalen-2-yl)-ethanone (commercially available) | 435.48 | 355.1 |
| 16 | 4-[4-(3-methoxy-phenyl)-thiazol-2-yl]-piperidine; hydrobromide | 4-thiocarbamoyl-piperidine-1-carboxylic acid tert-butyl ester (commercially available) and 2-bromo-1-(3-methoxy-phenyl)-ethanone (commercially available) | 355.3 | 275 |
| 17 | 4-(4-p-tolyl-thiazol-2-yl)-piperidine; hydrobromide | 4-thiocarbamoyl-piperidine-1-carboxylic acid tert-butyl ester (commercially available) and 2-bromo-1-(4-methyl-phenyl)-ethanone (commercially available) | 339.3 | 258.9 |
| 18 | 4-[4-(4-difluoromethoxy-phenyl)-thiazol-2-yl]-piperidine; hydrobromide | 4-thiocarbamoyl-piperidine-1-carboxylic acid tert-butyl ester (commercially available) and 2-bromo-1-(4-difluoromethoxy-phenyl)-ethanone (commercially available) | 391.28 | 311 |
| 19 | 4-[4-(2,3-dihydro-benzo[1,4]dioxin-6-yl)-thiazol-2-yl]-piperidine; hydrobromide | 4-thiocarbamoyl-piperidine-1-carboxylic acid tert-butyl ester (commercially available) and 2-bromo-1-(2,3-dihydro-benzo[1,4]dioxin-6-yl)-ethanone (commercially available) | 383.31 | 303.1 |
| 20 | 4-[4-(3,4-dihydro-2H-benzo[b][1,4]dioxepin-7-yl)-thiazol-2-yl]-piperidine; hydrobromide | 4-thiocarbamoyl-piperidine-1-carboxylic acid tert-butyl ester (commercially available) and 2-bromo-1-(3,4-dihydro-2H-benzo[b][1,4]dioxepin-7-yl)-ethanone (commercially available) | 397.34 | 317 |
| 21 | 3-(2-piperidin-4-yl-thiazol-4-yl)-benzonitrile; hydrobromide | 4-thiocarbamoyl-piperidine-1-carboxylic acid tert-butyl ester (commercially available) and 3-(2-bromo-acetyl)-benzonitrile (commercially available) | 350.29 | 270.1 |
| 22 | 4-[4-(4-pyrrolidin-1-yl-phenyl)-thiazol-2-yl]-piperidine; hydrobromide | 4-thiocarbamoyl-piperidine-1-carboxylic acid tert-butyl ester (commercially available) and 2-bromo-1-(4-pyrrolidin-1-yl-phenyl)-ethanone (commercially available) | 394.38 | 313.7 |
| 23 | 4-[4-(4-trifluoromethoxy-phenyl)-thiazol-2-yl]-piperidine; hydrobromide | 4-thiocarbamoyl-piperidine-1-carboxylic acid tert-butyl ester (commercially available) and 2-bromo-1-(4-trifluoromethoxy-phenyl)-ethanone (commercially available) | 409.27 | 329.4 |

TABLE 1-continued

| Intermediate | Name | Starting materials | MW | MH+ (-HBr) found [100%] |
|---|---|---|---|---|
| 24 | 4-[4-(3-trifluoromethyl-phenyl)-thiazol-2-yl]-piperidine; hydrobromide | 4-thiocarbamoyl-piperidine-1-carboxylic acid tert-butyl ester (commercially available) and 2-bromo-1-(3-trifluoromethyl-phenyl)-ethanone (commercially available) | 393.27 | 313.1 |
| 25 | 4-[4-(3,4-dimethoxy-phenyl)-thiazol-2-yl]-piperidine; hydrobromide | 4-thiocarbamoyl-piperidine-1-carboxylic acid tert-butyl ester (commercially available) and 2-bromo-1-(3,4-dimethoxy-phenyl)-ethanone (commercially available) | 385.33 | 305.3 |
| 26 | 4-(4-benzo[1,3]dioxol-5-yl-thiazol-2-yl)-piperidine; hydrobromide | 4-thiocarbamoyl-piperidine-1-carboxylic acid tert-butyl ester (commercially available) and 1-benzo[1,3]dioxol-5-yl-2-bromo-ethanone (commercially available) | 369.29 | 288.8 |
| 27 | 4-[4-(4-bromo-phenyl)-5-methyl-thiazol-2-yl]-piperidine; hydrobromide | 4-thiocarbamoyl-piperidine-1-carboxylic acid tert-butyl ester (commercially available) and 2-bromo-1-(4-bromo-phenyl)-propan-1-one (commercially available) | 418.2 | 339 |
| 28 | 4-(2-piperidin-4-yl-thiazol-4-yl)-pyridine; dihydrobromide | 4-thiocarbamoyl-piperidine-1-carboxylic acid tert-butyl ester (commercially available) and 2-bromo-1-pyridin-4-yl-ethanone (commercially available) | 407.18 | 246.1 |
| 29 | 4-(4-thiophen-3-yl-thiazol-2-yl)-piperidine; hydrobromide | 4-thiocarbamoyl-piperidine-1-carboxylic acid tert-butyl ester (commercially available) and 2-bromo-1-thiophen-3-yl-ethanone (commercially available) | 331.3 | 250.9 |
| 30 | 4-(4-thiophen-2-yl-thiazol-2-yl)-piperidine; hydrobromide | 4-thiocarbamoyl-piperidine-1-carboxylic acid tert-butyl ester (commercially available) and 2-bromo-1-thiophen-2-yl-ethanone (commercially available) | 331.3 | 250.9 |
| 31 | 4-[4-(3,4-dichloro-phenyl)-thiazol-2-yl]-piperidine; hydrobromide | 4-thiocarbamoyl-piperidine-1-carboxylic acid tert-butyl ester (commercially available) and 2-bromo-1-(3,4-dichloro-phenyl)-ethanone (commercially available) | 394.17 | 315 |
| 32 | 4-[4-(2,4-dimethoxy-phenyl)-thiazol-2-yl]-piperidine; hydrobromide | 4-thiocarbamoyl-piperidine-1-carboxylic acid tert-butyl ester (commercially available) and 2-bromo-1-(2,4-dimethoxy-phenyl)-ethanone (commercially available) | 385.33 | 305.1 |
| 33 | 4-[4-(3,5-bis-trifluoromethyl-phenyl)-thiazol-2-yl]-piperidine; hydrobromide | 4-thiocarbamoyl-piperidine-1-carboxylic acid tert-butyl ester (commercially available) and 2-bromo-1-(3,5-bis-trifluoromethyl-phenyl)-ethanone (commercially available) | 461.27 | 381.1 |

According to the procedure described for the synthesis of Example 1 further thiazole derivatives have been synthesized from the respective intermediate listed in Table 1 and the respective aldehyde or ketone mentioned in Table 2. In cases where the thiazole intermediates were reacted with ketones the reaction temperature was shifted from room temperature (used in the cases where thiazole intermediates were reacted with aldehydes) to 40° C. The examples are compiled in Table 2 and comprise Example 2 to Example 64.

TABLE 2

| Example No. | Name | Starting Materials | MW | MH+ found (100%) |
|---|---|---|---|---|
| 2 | 1-cyclopentyl-4-(4-phenyl-thiazol-2-yl)-piperidine | 4-(4-phenyl-thiazol-2-yl)-piperidine; hydrobromide (Intermediate 1) and cyclopentanone (commercially available) | 312.5 | 312.2 |
| 3 | 4-[4-(3,4-difluoro-phenyl)-thiazol-2-yl]-1-isobutyl-piperidine | 4-[4-(3,4-difluoro-phenyl)-thiazol-2-yl-piperidine; hydrobromide (Intermediate 2) and 2-methyl-propionaldehyde (commercially available) | 336.4 | 337.3 |
| 4 | 4-[4-(3,4-difluoro-phenyl)-thiazol-2-yl]-1-isopropyl-piperidine | 4-[4-(3,4-difluoro-phenyl)-thiazol-2-yl]-piperidine; hydrobromide (Intermediate 2) and acetone (commercially available) | 322.4 | 323.2 |
| 5 | 1-cyclopentyl-4-[4-(3,4-difluoro-phenyl)-thiazol-2-yl]-piperidine | 4-[4-(3,4-difluoro-phenyl)-thiazol-2-yl]-piperidine; hydrobromide (Intermediate 2) and cyclopentanone (commercially available) | 348.5 | 349.2 |
| 6 | 4-(4-cyclohexyl-thiazol-2-yl)-1-isobutyl-piperidine | 4-(4-cyclohexyl-thiazol-2-yl)-piperidine; hydrobromide (Intermediate 3) and 2-methyl-propionaldehyde (commercially available) | 306.5 | 307.3 |
| 7 | 4-(4-cyclohexyl-thiazol-2-yl)-1-cyclopentyl-piperidine | 4-(4-cyclohexyl-thiazol-2-yl)-piperidine; hydrobromide (Intermediate 3) and cyclopentanone (commercially available) | 318.5 | 319.1 |
| 8 | 1-isobutyl-4-[4-(4-methoxy-phenyl)-thiazol-2-yl]-piperidine | 4-[4-(4-methoxy-phenyl)-thiazol-2-yl]-piperidine; hydrobromide (Intermediate 4) and 2-methyl-propionaldehyde (commercially available) | 330.5 | 331.2 |
| 9 | 1-isopropyl-4-[4-(4-methoxy-phenyl)-thiazol-2-yl]-piperidine | 4-[4-(4-methoxy-phenyl)-thiazol-2-yl]-piperidine; hydrobromide (Intermediate 4) and acetone (commercially available) | 316.5 | 317.2 |
| 10 | 1-cyclopentyl-4-[4-(4-methoxy-phenyl)-thiazol-2-yl]-piperidine | 4-[4-(4-methoxy-phenyl)-thiazol-2-yl]-piperidine; hydrobromide (Intermediate 4) and cyclopentanone (commercially available) | 342.5 | 343.2 |
| 11 | 4-[4-(2-fluoro-4-methoxy-phenyl)-thiazol-2-yl]-1-isobutyl-piperidine | 4-[4-(2-fluoro-4-methoxy-phenyl)-thiazol-2-yl]-piperidine; hydrobromide (Intermediate 5) and 2-methyl-propionaldehyde (commercially available) | 348.5 | 349.3 |
| 12 | 4-[4-(2-fluoro-4-methoxy-phenyl)-thiazol-2-yl]-1-isopropyl-piperidine | 4-[4-(2-fluoro-4-methoxy-phenyl)-thiazol-2-yl]-piperidine; hydrobromide (Intermediate 5) and acetone (commercially available) | 334.5 | 335.3 |

TABLE 2-continued

| Example No. | Name | Starting Materials | MW | MH+ found (100%) |
|---|---|---|---|---|
| 13 | 1-cyclopentyl-4-[4-(2-fluoro-4-methoxy-phenyl)-thiazol-2-yl]-piperidine | 4-[4-(2-fluoro-4-methoxy-phenyl)-thiazol-2-yl]-piperidine; hydrobromide (Intermediate 5) and cyclopentanone (commercially available) | 360.5 | 361.2 |
| 14 | 1-isobutyl-4-[4-(2-methoxy-phenyl)-thiazol-2-yl]-piperidine | 4-[4-(2-methoxy-phenyl)-thiazol-2-yl]-piperidine; hydrobromide (Intermediate 6) and 2-methyl-propionaldehyde (commercially available) | 330.5 | 331.2 |
| 15 | 1-isopropyl-4-[4-(2-methoxy-phenyl)-thiazol-2-yl]-piperidine | 4-[4-(2-methoxy-phenyl)-thiazol-2-yl]-piperidine; hydrobromide (Intermediate 6) and acetone (commercially available) | 316.5 | 317.2 |
| 16 | 1-cyclopentyl-4-[4-(2-methoxy-phenyl)-thiazol-2-yl]-piperidine | 4-[4-(2-methoxy-phenyl)-thiazol-2-yl]-piperidine; hydrobromide (Intermediate 6) and cyclopentanone (commercially available) | 342.5 | 343.2 |
| 17 | 2-[2-(1-isobutyl-piperidin-4-yl)-thiazol-4-yl]-3-methyl-pyrazine | methyl-3-(2-piperidin-4-yl-thiazol-4-yl)-pyrazine; hydrobromide (Intermediate 7) and 2-methyl-propionaldehyde (commercially available) | 316.5 | 317.2 |
| 18 | 2-[2-(1-cyclopentyl-piperidin-4-yl)-thiazol-4-yl]-3-methyl-pyrazine | methyl-3-(2-piperidin-4-yl-thiazol-4-yl)-pyrazine; hydrobromide (Intermediate 7) and cyclopentanone (commercially available) | 328.5 | 329.3 |
| 19 | 1-isobutyl-4-[4-(2-trifluoromethyl-phenyl)-thiazol-2-yl]-piperidine | 4-[4-(2-trifluoromethyl-phenyl)-thiazol-2-yl]-piperidine; hydrobromide (Intermediate 8) and 2-methyl-propionaldehyde (commercially available) | 368.5 | 369.1 |
| 20 | 1-cyclopentyl-4-[4-(2-trifluoromethyl-phenyl)-thiazol-2-yl]-piperidine | 4-[4-(2-trifluoromethyl-phenyl)-thiazol-2-yl]-piperidine; hydrobromide (Intermediate 8) and cyclopentanone (commercially available) | 380.5 | 381.3 |
| 21 | 4-[4-(4-chloro-phenyl)-thiazol-2-yl]-1-isobutyl-piperidine | 4-[4-(4-chloro-phenyl)-thiazol-2-yl]-piperidine; hydrobromide (Intermediate 9) and 2-methyl-propionaldehyde (commercially available) | 334.9 | 335.3 |
| 22 | 4-[4-(4-chloro-phenyl)-thiazol-2-yl]-1-isopropyl-piperidine | 4-[4-(4-chloro-phenyl)-thiazol-2-yl]-piperidine; hydrobromide (Intermediate 9) and acetone (commercially available) | 320.9 | 321.1 |
| 23 | 4-[4-(4-chloro-phenyl)-thiazol-2-yl]-1-cyclopentyl-piperidine | 4-[4-(4-chloro-phenyl)-thiazol-2-yl]-piperidine; hydrobromide and cyclopentanone (commercially available) | 346.9 | 347.1 |
| 24 | 4-[4-(3-fluoro-phenyl)-thiazol-2-yl]-1-isobutyl-piperidine | 4-[4-(3-fluoro-phenyl)-thiazol-2-yl]-piperidine; hydrobromide (Intermediate 10) and 2-methyl-propionaldehyde (commercially available) | 318.5 | 319.2 |

TABLE 2-continued

| Example No. | Name | Starting Materials | MW | MH+ found (100%) |
|---|---|---|---|---|
| 25 | 4-[4-(3-fluoro-phenyl)-thiazol-2-yl]-1-isopropyl-piperidine | 4-[4-(3-fluoro-phenyl)-thiazol-2-yl]-piperidine; hydrobromide (Intermediate 10) and acetone (commercially available) | 304.4 | 305.2 |
| 26 | 1-cyclopentyl-4-[4-(3-fluoro-phenyl)-thiazol-2-yl]-piperidine | 4-[4-(3-fluoro-phenyl)-thiazol-2-yl]-piperidine; hydrobromide (Intermediate 10) and cyclopentanone (commercially available) | 330.5 | 331.2 |
| 27 | 1-cyclopentyl-4-(5-methyl-4-phenyl-thiazol-2-yl)-piperidine | 4-(5-methyl-4-phenyl-thiazol-2-yl)-piperidine; hydrobromide (Intermediate 11) and cyclopentanone (commercially available) | 326.5 | 327.2 |
| 28 | 4-[4-(2-fluoro-3-trifluoromethyl-phenyl)-thiazol-2-yl]-1-isopropyl-piperidine | 4-[4-(2-fluoro-3-trifluoromethyl-phenyl)-thiazol-2-yl]-piperidine; hydrobromide (Intermediate 12) and acetone (commercially available) | 372.4 | 373.1 |
| 29 | 4-[2-(1-isopropyl-piperidin-4-yl)-thiazol-4-yl]-benzonitrile | 4-(2-piperidin-4-yl-thiazol-4-yl)-benzonitrile; hydrobromide (Intermediate 13) and acetone (commercially available) | 311.5 | 312.3 |
| 30 | 1-isopropyl-4-[4-(4-trifluoromethyl-phenyl)-thiazol-2-yl]-piperidine | 4-[4-(4-trifluoromethyl-phenyl)-thiazol-2-yl]-piperidine; hydrobromide (Intermediate 14) and acetone (commercially available) | 354.4 | 355.3 |
| 31 | 1-isopropyl-4-[4-(3-methoxy-phenyl)-thiazol-2-yl]-piperidine | 4-[4-(3-methoxy-phenyl)-thiazol-2-yl]-piperidine; hydrobromide (Intermediate 16) and acetone (commercially available) | 316.5 | 317.2 |
| 32 | 1-isopropyl-4-(4-p-tolyl-thiazol-2-yl)-piperidine | 4-(4-p-tolyl-thiazol-2-yl)-piperidine; hydrobromide (Intermediate 17) and acetone (commercially available) | 300.5 | 301.3 |
| 33 | 4-[4-(4-difluoromethoxy-phenyl)-thiazol-2-yl]-1-isopropyl-piperidine | 4-[4-(4-difluoromethoxy-phenyl)-thiazol-2-yl]-piperidine; hydrobromide (Intermediate 18) and acetone (commercially available) | 352.4 | 353.2 |
| 34 | 4-[4-(2,3-dihydro-benzo[1,4]dioxin-6-yl)-thiazol-2-yl]-1-isopropyl-piperidine | 4-[4-(2,3-dihydro-benzo[1,4]dioxin-6-yl)-thiazol-2-yl]-piperidine (Intermediate 19); hydrobromide and acetone (commercially available) | 344.5 | 345.2 |
| 35 | 4-[4-(3,4-dihydro-2H-benzo[b][1,4]dioxepin-7-yl)-thiazol-2-yl]-1-isopropyl-piperidine | 4-[4-(3,4-dihydro-2H-benzo[b][1,4]dioxepin-7-yl)-thiazol-2-yl]-piperidine; hydrobromide (Intermediate 20) and acetone (commercially available) | 358.5 | 359.2 |
| 36 | 3-[2-(1-isopropyl-piperidin-4-yl)-thiazol-4-yl]-benzonitrile | 3-(2-piperidin-4-yl-thiazol-4-yl)-benzonitrile; hydrobromide (Intermediate 21) and acetone (commercially available) | 311.5 | 312.3 |

TABLE 2-continued

| Example No. | Name | Starting Materials | MW | MH+ found (100%) |
|---|---|---|---|---|
| 37 | 1-isopropyl-4-[4-(4-pyrrolidin-1-yl-phenyl)-thiazol-2-yl]-piperidine | 4-[4-(4-pyrrolidin-1-yl-phenyl)-thiazol-2-yl]-piperidine; hydrobromide (Intermediate 22) and acetone (commercially available) | 355.5 | 356.4 |
| 38 | 1-isopropyl-4-[4-(4-trifluoromethoxy-phenyl)-thiazol-2-yl]-piperidine | 4-[4-(4-trifluoromethoxy-phenyl)-thiazol-2-yl]-piperidine; hydrobromide (Intermediate 23) and acetone (commercially available) | 370.4 | 371.2 |
| 39 | 1-isopropyl-4-[4-(3-trifluoromethyl-phenyl)-thiazol-2-yl]-piperidine | 4-[4-(3-trifluoromethyl-phenyl)-thiazol-2-yl]-piperidine; hydrobromide (Intermediate 24) and acetone (commercially available) | 354.4 | 355.3 |
| 40 | 4-[4-(3,4-dimethoxy-phenyl)-thiazol-2-yl]-1-isopropyl-piperidine | 4-[4-(3,4-dimethoxy-phenyl)-thiazol-2-yl]-piperidine; hydrobromide (Intermediate 25) and acetone (commercially available) | 346.5 | 347.2 |
| 41 | 4-(4-benzo[1,3]dioxol-5-yl-thiazol-2-yl)-1-isopropyl-piperidine | 4-(4-benzo[1,3]dioxol-5-yl-thiazol-2-yl)-piperidine; hydrobromide (Intermediate 26) and acetone (commercially available) | 330.5 | 331.2 |
| 42 | 4-[4-(4-bromo-phenyl)-5-methyl-thiazol-2-yl]-1-isopropyl-piperidine | 4-[4-(4-bromo-phenyl)-5-methyl-thiazol-2-yl]-piperidine; hydrobromide (Intermediate 27) and acetone (commercially available) | 379.4 | 379.2 |
| 43 | 1-isopropyl-4-(4-thiophen-3-yl-thiazol-2-yl)-piperidine | 4-(4-thiophen-3-yl-thiazol-2-yl)-piperidine; hydrobromide (Intermediate 29) and acetone (commercially available) | 292.5 | 293.2 |
| 44 | 1-isopropyl-4-(4-thiophen-2-yl-thiazol-2-yl)-piperidine | 4-(4-thiophen-2-yl-thiazol-2-yl)-piperidine; hydrobromide (Intermediate 30) and acetone (commercially available) | 292.5 | 293.2 |
| 45 | 4-[4-(3,4-dichloro-phenyl)-thiazol-2-yl]-1-isopropyl-piperidine | 4-[4-(3,4-dichloro-phenyl)-thiazol-2-yl]-piperidine; hydrobromide (Intermediate 31) and acetone (commercially available) | 355.3 | 355.2 |
| 46 | 4-[4-(2,4-dimethoxy-phenyl)-thiazol-2-yl]-1-isopropyl-piperidine | 4-[4-(2,4-dimethoxy-phenyl)-thiazol-2-yl]-piperidine; hydrobromide (Intermediate 32) and acetone (commercially available) | 346.5 | 347.1 |
| 47 | 4-[2-(1-cyclopentyl-piperidin-4-yl)-thiazol-4-yl]-benzonitrile | 4-(2-piperidin-4-yl-thiazol-4-yl)-benzonitrile; hydrobromide (Intermediate 13) and cyclopentanone (commercially available) | 337.5 | 338.3 |
| 48 | 1-cyclopentyl-4-[4-(4-trifluoromethyl-phenyl)-thiazol-2-yl]-piperidine | 4-[4-(4-trifluoromethyl-phenyl)-thiazol-2-yl]-piperidine; hydrobromide (Intermediate 14) and cyclopentanone (commercially available) | 380.5 | 381.3 |

TABLE 2-continued

| Example No. | Name | Starting Materials | MW | MH+ found (100%) |
|---|---|---|---|---|
| 49 | 1-cyclopentyl-4-[4-(5,5,8,8-tetramethyl-5,6,7,8-tetrahydro-naphthalen-2-yl)-thiazol-2-yl]-piperidine | 4-[4-(5,5,8,8-tetramethyl-5,6,7,8-tetrahydro-naphthalen-2-yl)-thiazol-2-yl]-piperidine; hydrobromide (Intermediate 15) and cyclopentanone (commercially available) | 422.7 | 423.3 |
| 50 | 1-cyclopentyl-4-[4-(3-methoxy-phenyl)-thiazol-2-yl]-piperidine | 4-[4-(3-methoxy-phenyl)-thiazol-2-yl]-piperidine; hydrobromide (Intermediate 16) and cyclopentanone (commercially available) | 342.5 | 343.1 |
| 51 | 1-cyclopentyl-4-[4-(4-difluoromethoxy-phenyl)-thiazol-2-yl]-piperidine | 4-[4-(4-difluoromethoxy-phenyl)-thiazol-2-yl]-piperidine; hydrobromide (Intermediate 18) and cyclopentanone (commercially available) | 378.5 | 379.3 |
| 52 | 1-cyclopentyl-4-[4-(2,3-dihydro-benzo[1,4]dioxin-6-yl)-thiazol-2-yl]-piperidine | 4-[4-(2,3-dihydro-benzo[1,4]dioxin-6-yl)-thiazol-2-yl]-piperidine; hydrobromide (Intermediate 19) and cyclopentanone (commercially available) | 370.5 | 371.1 |
| 53 | 1-cyclopentyl-4-[4-(3,4-dihydro-2H-benzo[b][1,4]dioxepin-7-yl)-thiazol-2-yl]-piperidine | 4-[4-(3,4-dihydro-2H-benzo[b][1,4]dioxepin-7-yl)-thiazol-2-yl]-piperidine; hydrobromide (Intermediate 20) and cyclopentanone (commercially available) | 384.5 | 385.2 |
| 54 | 3-[2-(1-cyclopentyl-piperidin-4-yl)-thiazol-4-yl]-benzonitrile | 3-(2-piperidin-4-yl-thiazol-4-yl)-benzonitrile; hydrobromide (Intermediate 21) and cyclopentanone (commercially available) | 337.5 | 338.3 |
| 55 | 1-cyclopentyl-4-[4-(4-trifluoromethoxy-phenyl)-thiazol-2-yl]-piperidine | 4-[4-(4-trifluoromethoxy-phenyl)-thiazol-2-yl]-piperidine; hydrobromide (Intermediate 23) and cyclopentanone (commercially available) | 396.5 | 397.3 |
| 56 | 1-cyclopentyl-4-[4-(3-trifluoromethyl-phenyl)-thiazol-2-yl]-piperidine | 4-[4-(3-trifluoromethyl-phenyl)-thiazol-2-yl]-piperidine; hydrobromide (Intermediate 24) and cyclopentanone (commercially available) | 380.5 | 381.3 |
| 57 | 1-cyclopentyl-4-[4-(3,4-dimethoxy-phenyl)-thiazol-2-yl]-piperidine | 4-[4-(3,4-dimethoxy-phenyl)-thiazol-2-yl]-piperidine; hydrobromide (Intermediate 25) and cyclopentanone (commercially available) | 372.5 | 373.1 |
| 58 | 4-(4-benzo[1,3]dioxol-5-yl-thiazol-2-yl)-1-cyclopentyl-piperidine | 4-(4-benzo[1,3]dioxol-5-yl-thiazol-2-yl)-piperidine; hydrobromide (Intermediate 26) and cyclopentanone (commercially available) | 356.5 | 357.2 |
| 59 | 4-[4-(4-bromo-phenyl)-5-methyl-thiazol-2-yl]-1-cyclopentyl-piperidine | 4-[4-(4-bromo-phenyl)-5-methyl-thiazol-2-yl]-piperidine; hydrobromide (Intermediate 27) and cyclopentanone (commercially available) | 405.4 | 405.3 |
| 60 | 4-[2-(1-cyclopentyl-piperidin-4-yl)-thiazol-4-yl]-pyridine | 4-(2-piperidin-4-yl-thiazol-4-yl)-pyridine; dihydrobromide (Intermediate 28) and cyclopentanone (commercially available) | 313.5 | 314.2 |

TABLE 2-continued

| Example No. | Name | Starting Materials | MW | MH+ found (100%) |
|---|---|---|---|---|
| 61 | 1-cyclopentyl-4-(4-thiophen-3-yl-thiazol-2-yl)-piperidine | 4-(4-thiophen-3-yl-thiazol-2-yl)-piperidine; hydrobromide (Intermediate 29) and cyclopentanone (commercially available) | 318.5 | 319.2 |
| 62 | 1-cyclopentyl-4-[4-(3,4-dichloro-phenyl)-thiazol-2-yl]-piperidine | 4-[4-(3,4-dichloro-phenyl)-thiazol-2-yl]-piperidine; hydrobromide (Intermediate 31) and cyclopentanone (commercially available) | 381.4 | 381 |
| 63 | 1-cyclopentyl-4-[4-(2,4-dimethoxy-phenyl)-thiazol-2-yl]-piperidine | 4-[4-(2,4-dimethoxy-phenyl)-thiazol-2-yl]-piperidine; hydrobromide (Intermediate 32) and cyclopentanone (commercially available) | 372.5 | 373.1 |
| 64 | 4-[4-(3,5-bis-trifluoromethyl-phenyl)-thiazol-2-yl]-1-cyclopentyl-piperidine | 4-[4-(3,5-bis-trifluoromethyl-phenyl)-thiazol-2-yl]-piperidine; hydrobromide (Intermediate 33) and cyclopentanone (commercially available) | 448.5 | 449.2 |

Example 65

2-(1-Isopropyl-piperidin-4-yl)-thiazole-4-carboxylic acid (4-chloro-phenyl)-amide Step 1: 2-Piperidin-4-yl-thiazole-4-carboxylic acid ethyl ester A mixture of 10 g (41 mmol) 4-thiocarbamoyl-piperidine-1-carboxylic acid tert-butyl ester (commercially available) and 7.98 g (41 mmol) ethyl bromopyruvate (commercially available) in 120 ml ethanol was stirred at 70° C. for 90 min. The mixture was evaporated to dryness, Na$_2$CO$_3$ aq. was added and the residue was extracted with ethyl acetate. The organic phases were washed with NaCl aq., dried with MgSO$_4$ and evaporated to dryness. The residue was purified on silica eluting with DCM/MeOH/25% NH$_3$ in water 100/20/1 to yield after evaporation of the product fractions 7.28 g (74%) of the title compound as light brown solid.

Step 2: 2-(1-Isopropyl-piperidin-4-yl)-thiazole-4-carboxylic acid ethyl ester

A mixture of 2 g (8.3 mmol) 2-piperidin-4-yl-thiazole-4-carboxylic acid ethyl ester, 0.67 g acetone, 1.2 ml acetic acid and 2.47 g (11.6 mmol) sodium triacetoxyborohydride in 20 ml THF was stirred at 40° C. for 18 h. After evaporation to dryness the residue was extracted with 3×250 ml ethyl acetate and the combined organic phases were washed with 2×NaHCO$_3$, NaCl aq., dried with MgSO$_4$ and evaporated to yield 1.9 g (83%) of the title compound of orange solid. (m/e): 283.0 (MH+; 100%).

Step 3: 2-(1-Isopropyl-piperidin-4-yl)-thiazole-4-carboxylic acid; hydrochloride A mixture of 1.9 g (6.7 mmol) 2-(1-Isopropyl-piperidin-4-yl)-thiazole-4-carboxylic acid ethyl ester and 5.7 ml HCl aq. (37%) in 13 ml water was stirred at 95° C. for 21 h. The mixture was evaporated to dryness and used without further purification in the consecutive step. (m/e): 255.3 (MH(−HCl)+; 100%).

Step 4: 2-(1-Isopropyl-piperidin-4-yl)-thiazole-4-carboxylic acid (4-chloro-phenyl)-amide A mixture of 29.1 mg (0.1 mmol) 2-(1-isopropyl-piperidin-4-yl)-thiazole-4-carboxylic acid; hydrochloride, 35.3 mg (0.11 mmol) 2-(1H-benzotriazol-1-yl-1,1,3,3-tetramethyl uronium tetrafluoroborate, 14.03 mg (0.11 mol) 4-chloroaniline and 140 ul (0.5 mmol) N-ethyldiisopropylamine in 1 ml DMF was reacted at room temperature for a prolonged period of time. The mixture was treated with 50 µl triethylamine and subjected to preparative HPLC purification on reversed phase material eluting with a gradient of acetonitrile/water/triethyamine (0.05%). The product fractions were evaporated to dryness to yield 10.6 mg (29%) of the title compound. MS (m/e): 364.1 (MH+, 100%).

Example 66

[2-(1-Cyclopentyl-piperidin-4-yl)-thiazol-4-yl]-(2-methyl-pyrrolidin-1-yl)-methanone Step 1: 2-(1-Cyclopentyl-piperidin-4-yl)-thiazole-4-carboxylic acid ethyl ester According to the procedure described for the synthesis of Example 65b (step 2, (2-(1-isopropyl-piperidin-4-yl)-thiazole-4-carboxylic acid ethyl ester) the title compound was synthesized from 2-piperidin-4-yl-thiazole-4-carboxylic acid ethyl ester and cyclopentanone (commercially available). MS (m/e): 309.3 (MH+, 100%).

Step 2: 2-(1-Cyclopentyl-piperidin-4-yl)-thiazole-4-carboxylic acid

According to the procedure described for the synthesis of Example 65c (step 3, (2-(1-isopropyl-piperidin-4-yl)-thiazole-4-carboxylic acid) the title compound was synthesized from 2-piperidin-4-yl-thiazole-4-carboxylic acid ethyl ester. MS (m/e): 281.0 (MH$^+$, 100%).

Step 3: [2-(1-Cyclopentyl-piperidin-4-yl)-thiazol-4-yl]-(2-methyl-pyrrolidin-1-yl)-methanone According to the procedure described for the synthesis of Example 65d (step 4, 2-(1-isopropyl-piperidin-4-yl)-thiazole-4-carboxylic acid (4-chloro-phenyl)-amide) the title compound was synthesized from 2-(1-cyclopentyl-piperidin-4-yl)-thiazole-4-carboxylic acid and 2-methylpyrrolidine. MS (m/e): 348.4 (MH$^+$, 100%).

According to the procedure described for the synthesis of Example 66 further thiazole amide derivatives have been synthesized from 2-(1-cyclopentyl-piperidin-4-yl)-thiazole-4-carboxylic acid and the respective amine mentioned in Table 3. The examples are compiled in Table 3 and comprise example 67 to example 73.

-continued

| Ingredients | Per tablet | |
|---|---|---|
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

TABLE 3

| Example No. | Name | Starting Materials | MW | MH$^+$ found (100%) |
|---|---|---|---|---|
| 67 | [2-(1-cyclopentyl-piperidin-4-yl)-thiazol-4-yl]-(3-methyl-piperidin-1-yl)-methanone | 2-(1-cyclopentyl-piperidin-4-yl)-thiazole-4-carboxylic acid and 3-methyl-piperidine (commercially available) | 361.6 | 362.3 |
| 68 | [2-(1-cyclopentyl-piperidin-4-yl)-thiazol-4-yl]-(2-methyl-piperidin-1-yl)-methanone | 2-(1-cyclopentyl-piperidin-4-yl)-thiazole-4-carboxylic acid and 2-methyl-piperidine (commercially available) | 361.6 | 362.3 |
| 69 | azepan-1-yl-[2-(1-cyclopentyl-piperidin-4-yl)-thiazol-4-yl]-methanone | 2-(1-cyclopentyl-piperidin-4-yl)-thiazole-4-carboxylic acid and azepane (commercially available) | 361.6 | 362.3 |
| 70 | [2-(1-cyclopentyl-piperidin-4-yl)-thiazol-4-yl]-(3,4-dihydro-1H-isoquinolin-2-yl)-methanone | 2-(1-cyclopentyl-piperidin-4-yl)-thiazole-4-carboxylic acid and 3,4-dihydro-1H-isoquinoline (commercially available) | 395.6 | 396.3 |
| 71 | 2-(1-cyclopentyl-piperidin-4-yl)-thiazole-4-carboxylic acid phenylamide | 2-(1-cyclopentyl-piperidin-4-yl)-thiazole-4-carboxylic acid and aniline (commercially available) | 355.5 | 356.3 |
| 72 | 2-(1-cyclopentyl-piperidin-4-yl)-thiazole-4-carboxylic acid (4-chloro-phenyl)-amide | 2-(1-cyclopentyl-piperidin-4-yl)-thiazole-4-carboxylic acid and 4-chloroaniline (commercially available) | 389.9 | 390.2 |
| 73 | 2-(1-cyclopentyl-piperidin-4-yl)-thiazole-4-carboxylic acid (3-methoxy-phenyl)-amide | 2-(1-cyclopentyl-piperidin-4-yl)-thiazole-4-carboxylic acid and 3-methoxyaniline (commercially available) | 385.5 | 386.3 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of the formula:

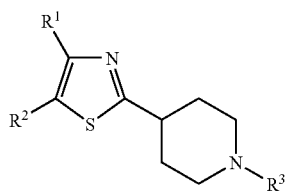

or a pharmaceutically acceptable salt thereof, wherein:
$R^1$ is phenyl unsubstituted or substituted with one or two groups independently selected from the group consisting of lower alkyl, halogen, lower halogenalkyl, lower alkoxy, lower halogenalkoxy, cyano, pyrrolidinyl and lower hydroxyalkyl,
$R^2$ is hydrogen or lower alkyl; and
$R^3$ is isobutyl or cycloalkyl.

2. A compound according to claim 1, wherein $R^1$ is phenyl substituted with one or two groups independently selected from the group consisting of lower alkyl, halogen, lower halogenalkyl, lower alkoxy, lower halogenalkoxy, and cyano.

3. A compound according to claim 1, wherein $R^1$ is phenyl substituted with one or two groups independently selected from the group consisting of halogen, lower halogenalkyl, lower alkoxy, lower halogenalkoxy, and cyano.

4. A compound according to claim 1, wherein $R^1$ is phenyl substituted with one or two groups independently selected from the group consisting of halogen, lower halogenalkyl, lower alkoxy, and lower halogenalkoxy.

5. A compound according to claim 1, wherein $R^1$ is phenyl substituted with one or two groups independently selected from the group consisting of halogen, lower alkoxy, and lower halogenalkoxy.

6. A compound according to claim 1, wherein $R^1$ is phenyl substituted with one or two groups independently selected from the group consisting of halogen and lower alkoxy.

7. A compound according to claim 1, wherein $R^1$ is phenyl substituted with one or two groups independently selected from the group consisting of fluoro, chloro, bromo, methoxy, trifluoromethyl, difluoromethoxy, trifluoromethoxy, and cyano.

8. A compound according to claim 1, wherein $R^2$ is hydrogen.

9. A compound according to claim 1, wherein $R^2$ is lower alkyl.

10. A compound according to claim 1, wherein $R^3$ is isobutyl.

11. A compound according to claim 1, wherein $R^3$ is cycloalkyl.

12. A compound according to claim 1, wherein $R^3$ is cyclopentyl.

13. A compound according to claim 1, selected from the group consisting of:
1-cyclopentyl-4-(4-phenyl-thiazol-2-yl)-piperidine,
4-[4-(3,4-difluoro-phenyl)-thiazol-2-yl]-1-isobutyl-piperidine, 1-cyclopentyl-4-[4-(3,4-difluoro-phenyl)-thiazol-2-yl]-piperidine,
1-isobutyl-4-[4-(4-methoxy-phenyl)-thiazol-2-yl]-piperidine,
1-cyclopentyl-4-[4-(4-methoxy-phenyl)-thiazol-2-yl]-piperidine,
4-[4-(2-fluoro-4-methoxy-phenyl)-thiazol-2-yl]-1-isobutyl-piperidine,
1-cyclopentyl-4-[4-(2-fluoro-4-methoxy-phenyl)-thiazol-2-yl]-piperidine,
1-isobutyl-4-[4-(2-methoxy-phenyl)-thiazol-2-yl]-piperidine,
1-cyclopentyl-4-[4-(2-methoxy-phenyl)-thiazol-2-yl]-piperidine,
1-isobutyl-4-[4-(2-trifluoromethyl-phenyl)-thiazol-2-yl]-piperidine,
1-cyclopentyl-4-[4-(2-trifluoromethyl-phenyl)-thiazol-2-yl]-piperidine,
4-[4-(4-chloro-phenyl)-thiazol-2-yl]-1-isobutyl-piperidine,
4-[4-(4-chloro-phenyl)-thiazol-2-yl]-1-cyclopentyl-piperidine,
4-[4-(3-fluoro-phenyl)-thiazol-2-yl]-1-isobutyl-piperidine,
1-cyclopentyl-4-[4-(3-fluoro-phenyl)-thiazol-2-yl]-piperidine,
1-cyclopentyl-4-(5-methyl-4-phenyl-thiazol-2-yl)-piperidine,
4-[2-(1-cyclopentyl-piperidin-4-yl)-thiazol-4-yl]-benzonitrile,
1-cyclopentyl-4-[4-(4-trifluoromethyl-phenyl)-thiazol-2-yl]-piperidine,
1-cyclopentyl-4-[4-(3-methoxy-phenyl)-thiazol-2-yl]-piperidine,
1-cyclopentyl-4-[4-(4-difluoromethoxy-phenyl)-thiazol-2-yl]-piperidine,
3-[2-(1-cyclopentyl-piperidin-4-yl)-thiazol-4-yl]-benzonitrile,
1-cyclopentyl-4-[4-(4-trifluoromethoxy-phenyl)-thiazol-2-yl]-piperidine,
1-cyclopentyl-4-[4-(3-trifluoromethyl-phenyl)-thiazol-2-yl]-piperidine,
1-cyclopentyl-4-[4-(3,4-dimethoxy-phenyl)-thiazol-2-yl]-piperidine,
4-[4-(4-bromo-phenyl)-5-methyl-thiazol-2-yl]-1-cyclopentyl-piperidine,
1-cyclopentyl-4-[4-(3,4-dichloro-phenyl)-thiazol-2-yl]-piperidine,
1-cyclopentyl-4-[4-(2,4-dimethoxy-phenyl)-thiazol-2-yl]-piperidine, and
4-[4-(3,5-bis-trifluoromethyl-phenyl)-thiazol-2-yl]-1-cyclopentyl-piperidine,
or a pharmaceutically acceptable salt thereof.

14. A compound according to claim 1, selected from the group consisting of:
1-cyclopentyl-4-[4-(4-methoxy-phenyl)-thiazol-2-yl]-piperidine,
1-cyclopentyl-4-[4-(2-fluoro-4-methoxy-phenyl)-thiazol-2-yl]-piperidine,
1-cyclopentyl-4-[4-(2-methoxy-phenyl)-thiazol-2-yl]-piperidine,
4-[4-(4-chloro-phenyl)-thiazol-2-yl]-1-cyclopentyl-piperidine,
1-cyclopentyl-4-[4-(4-difluoromethoxy-phenyl)-thiazol-2-yl]-piperidine,
4-[4-(4-bromo-phenyl)-5-methyl-thiazol-2-yl]-1-cyclopentyl-piperidine, and
1-cyclopentyl-4-[4-(2,4-dimethoxy-phenyl)-thiazol-2-yl]-piperidine,
or a pharmaceutically acceptable salt thereof.

15. A process for the manufacture of a compound according to claim 1, comprising the steps of:
reacting a compound of the formula II

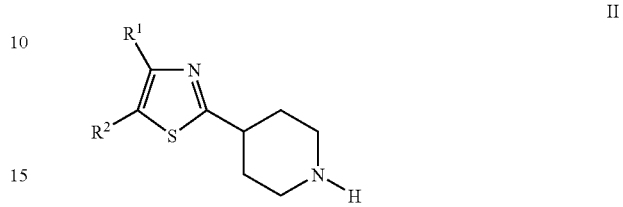

wherein $R^1$ and $R^2$ are as defined in claim 1, with an aldehyde or ketone of the formula III

R'R''C=O          III wherein R' is $C_1$-$C_7$-alkyl and R'' is $C_1$-$C_6$-alkyl or hydrogen or wherein R' and R'' together with the C atom they are attached to form a cycloalkyl ring,
to obtain a compound of the formula I

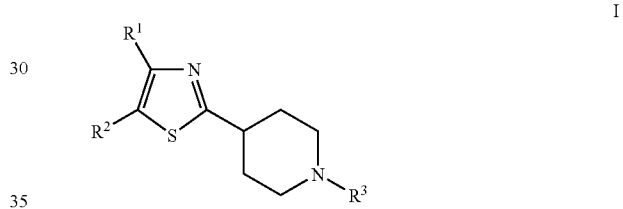

wherein $R^1$, $R^2$ and $R^3$ are as defined in claim 1,
and if desired,
converting the compound obtained into a pharmaceutically acceptable salt.

16. A pharmaceutical composition, comprising a therapeutically effective amount of a compound according to claim 1 and a pharmaceutically acceptable carrier or adjuvant.

17. A compound selected from the group consisting of:
4-[4-(3,4-difluoro-phenyl)-thiazol-2-yl]-1-isopropyl-piperidine,
4-[4-(2-fluoro-4-methoxy-phenyl)-thiazol-2-yl]-1-isopropyl-piperidine
1-isopropyl-4-[4-(2-methoxy-phenyl)-thiazol-2-yl]-piperidine,
4-[4-(2-fluoro-3-trifluoromethyl-phenyl)-thiazol-2-yl]-1-isopropyl-piperidine,
4-[2-(1-isopropyl-piperidin-4-yl)-thiazol-4-yl]-benzonitrile,
1-isopropyl-4-[4-(4-trifluoromethyl-phenyl)-thiazol-2-yl]-piperidine,
1-isopropyl-4-[4-(3-methoxy-phenyl)-thiazol-2-yl]-piperidine,
4-[4-(4-difluoromethoxy-phenyl)-thiazol-2-yl]-1-isopropyl-piperidine,
3-[2-(1-isopropyl-piperidin-4-yl)-thiazol-4-yl]-benzonitrile,
1-isopropyl-4-[4-(4-pyrrolidin-1-yl-phenyl)-thiazol-2-yl]-piperidine,
1-isopropyl-4-[4-(4-trifluoromethoxy-phenyl)-thiazol-2-yl]-piperidine, 1-isopropyl-4-[4-(3-trifluoromethyl-phenyl)-thiazol-2-yl]-piperidine, 4-[4-(3,4-dimethoxy-phenyl)-thiazol-2-yl]-1-isopropyl-piperidine, 4-[4-(4-bromo-phenyl)-5-methyl-thiazol-2-yl]-1-isopropyl-piperidine, 4-[4-(3,4-dichloro-phenyl)-thiazol-2-yl]-1-isopropyl-piperidine, and 4-[4-(2,4-dimethoxy-phenyl)-thiazol-2-yl]-1-isopropyl-piperidine, or a pharmaceutically acceptable salt thereof.

\* \* \* \* \*